United States Patent [19]

Atkins et al.

[11] B 3,992,456

[45] Nov. 16, 1976

[54] SYNTHESIS OF ALKADIENOLS

[75] Inventors: Kenneth Earl Atkins, South Charleston; Robert Michael Manyik, St. Albans; George Lawrence O'Connor, Charleston, all of W. Va.

[73] Assignee: Union Carbide Corporation, New York, N.Y.

[22] Filed: Feb. 27, 1975

[21] Appl. No.: 553,584

[44] Published under the second Trial Voluntary Protest Program on February 17, 1976 as document No. B 553,584.

Related U.S. Application Data

[63] Continuation of Ser. No. 816,792, April 16, 1969, abandoned.

[52] U.S. Cl. .................. 260/632 R; 260/614 AA; 260/633; 260/677 R
[51] Int. Cl.² ................................. C07C 33/02
[58] Field of Search ................. 260/632 R

[56] References Cited
UNITED STATES PATENTS

| | | | |
|---|---|---|---|
| 3,008,943 | 11/1961 | Guyer | 260/683.15 D |
| 3,361,840 | 1/1968 | Kohll et al. | 260/683.15 D |
| 3,365,498 | 1/1968 | Bryant et al. | 260/586 |
| 3,379,706 | 4/1968 | Wilke | 260/683.15 D |
| 3,407,224 | 10/1968 | Smutny | 260/497 A |
| 3,454,538 | 7/1969 | Naarmann et al. | 260/683.15 D |
| 3,499,042 | 3/1970 | Smutny | 260/632 R |
| 3,518,315 | 6/1970 | Smutny | 260/632 R |
| 3,534,088 | 10/1970 | Bryant et al. | 260/632 R |
| 3,670,032 | 6/1972 | Romanelli | 260/632 R |

*Primary Examiner*—Joseph E. Evans
*Attorney, Agent, or Firm*—Charles J. Metz

[57] ABSTRACT

Alkadienols are prepared by reacting a conjugated diolefin, such as butadiene, with water in the presence of palladium or platinum catalyst and in the presence of solvents. The addition of carbon dioxide to the reaction mixture greatly increases the yield of alkadienols. The products can be hydrogenated to saturated alcohols, useful for making plasticizers.

29 Claims, No Drawings

SYNTHESIS OF ALKADIENOLS

This is a continuation, of application Ser. No. 816,792 filed Apr. 16, 1969 now abandoned.

This invention relates to a method for making octadienyl alcohols which are useful as chemical intermediates to make octyl alcohols and esters. The octadienyl alcohols are also useful as chemical intermediates to make materials which find application in electroplating, plastics, perfumes and pharmaceuticals.

Octyl alcohols are useful as intermediates for making plasticizers, such as dioctyl phthalate which is widely used as a plasticizer for vinyl resins. 2-Ethylhexanol is the octyl alcohol most commonly used industrially for this purpose. However, n-octylalcohol would be preferable because plasticizers made from it are somewhat superior in their effectiveness. However, as of now, the available syntheses of n-octanol all leave room for improvement. The Ziegler synthesis of alcohols from ethylene gives a mixture of products of varying chain lengths, and heptene-1 required for an Oxo synthesis of octanols is not readily available and, furthermore, the Oxo processes also produce branchedchain alcohols. The best process known involves the dimerization of butadiene with carboxylic acids in the presence of palladium catalysts to yield octadienylcarboxylates which can be hydrolyzed and hydrogenated to n-octanol.

According to this invention, it has been found that under the appropriate catalytic and reaction conditions butadiene and water will react to yield octadienol which can be hydrogenated to octyl alcohol or further reacted to other useful materials. The reaction can be carried out in good efficiencies, and since this eliminates a step from the best previous synthesis, it is a more economic synthesis of octanol.

The reaction of two molecules of butadiene with compounds such as carboxylic acids to form octadienylcarboxylates using palladium and platinum catalysts is known. Processes of this nature are described in J. E. McKeon and D. R. Bryant application Ser. No. 660,226 filed Aug. 14, 1967 now U.S. Pat. No. 3,534,088 and R. M. Manyik and W. E. Walker application Ser. No. 757,485 filed Sept. 4, 1968 now U.S. Pat. No. 3,711,534. The most obvious industrial purpose of this reaction is to convert the octadienylcarboxylates into n-octanol, an intermediate for making plasticizers. This can be accomplished by hydrolyzing and hydrogenating the carboxylates.

According to this invention, it has been discovered that butadiene and water can be reacted in the presence of a palladium or platinum catalyst under appropriate reaction conditions to yield octadienol as a direct product. Generally our reaction conditions include the use of a solvent sufficient to maintain a homogeneous liquid reaction mixture containing a conjugated diene and water. This is achieved by the use of a solvent which has at least some degree of affinity for both the diene and water, as exemplified by solvents such as dioxane, dimethylacetamide, t-butanol, and acetone.

Not all solvents, however, are of equal effectiveness and it has been found that the lower alcohols such as ethanol, isopropanol, isobutanol, secondary butanol are more effective solvents for the reaction. Moreover, the primary and secondary alcohols are themselves capable of reacting to form alkoxy octadienes, and these appear to be effective co-reactants in also promoting the reaction of butadiene with water, particularly when employed in the presence of a non-reactive solvent such as dioxane. When the alcohol is used as a co-reactant, it is desirably used in a molar quantity of about 0.01:1 mole of alcohol per mole of water.

By the use of the alcohol as co-reactants, yields of octadienol of the order of 20 to 30 percent based on the butadiene charged have been obtained. However, when inert solvents alone are present, the yields of octadienol are seldom higher than 10 percent, and considerable amounts of octatriene, produced from the dimerization of the butadiene, are obtained.

Our invention, however, includes an important discovery whereby the results obtained in any of the solvent-assisted reactions of conjugated dienes and water can be dramatically increased. It has been discovered that when carbon dioxide or sulfur dioxide is added to the reaction mixture, a dramatic increase in the yield of octadienols is obtained.

For example, when a mixture of carbon dioxide, water, butadiene, dioxane solvent and palladium catalyst is reacted under certain conditions, a 50–60 percent yield of octadienol is realized compared to the 10 percent yield of octadienol that is obtained in the absence of carbon dioxide. In t-butanol solvent, a mixture of water, carbon dioxide, butadiene, solvent and catalyst yields at least 70 percent octadienol compared to a 10 percent yield in the absence of carbon dioxide. The total reaction is outlined below.

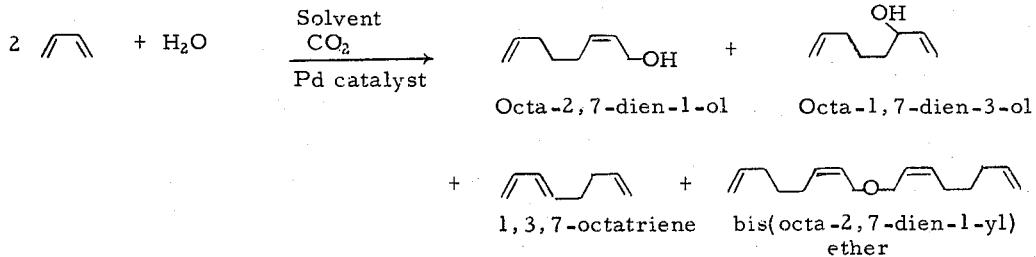

The precise effect of the carbon dioxide in assisting the reaction is not clearly understood, but it does not appear to be a co-reactant since it can be recovered at the end of the reaction. Furthermore, it has been observed that the effect of carbon dioxide appears to be independent of its molar ratio to either the diene or water. The initial molar ratios which are applicable to the invention can vary over a wide range. The carbon dioxide: diene ratio can vary from 0.001 or lower to 1000 or higher with 0.01 to 25.0 being preferred with 0.05 to 5.0 being especially preferred.

The water content of the reaction mixture is always a significant amount needed to react with the diene and will normally be over four percent and usually in the range of five to twenty percent by weight of the reaction mixture. In terms of molar ratios, the water:conjugated diene ratio can vary from 0.1 or lower to 1000 or higher with 0.5 to 10.0 being preferred and 1.0 to 5.0 being especially preferred. The amount of solvent used is a function of the reaction conditions, the molar ratios of reactanats, and certain other conditions. In some instances no solvent is required to achieve the desired reaction. Purified butadiene need not be used and instead the $C_4$ stream from an olefin plant, the usual feed to a butadiene refinery, can be employed in the reaction.

When this novel process is conducted as a homogeneous liquid phase reaction, the active catalyst species can be derived from a palladium compound which is soluble in the reaction mixture or which can be dissolved therein by reaction with one of the components of the said mixture.

Illustrative palladium compounds which may be used are those such as: palladium (II) acetylacetonate, palladium-olefin complexes such as 1,5-cyclooctadiene palladium (II) chloride, $\pi$-allylpalladium acetate, endodicyclopentadiene-palladium (II) bromide and the like; complexes of palladium with trihydrocarbylphosphines and arsines, e.g., bis(triphenylphosphine) palladium (II) acetate, bis(p-methoxyphenyl) palladium (II) acetate, tetrakis(triphenylphosphine) palladium (O), tetrakis(dimethylphenylphosphine) palladium (O), tetrakis(trinaphthylphosphine)palladium (O), tetrakis(tri-p-methoxyphosphine) palladium (O), tetrakis(diphenyl p-chlorophenylphosphine) palladium (O), bis(triphenylphosphine) palladium (II) nitrate, bis(triphenylarsine) palladium (II) chloride, bis(dimethylphenylphosphine) palladium (II) chloride, bis(trinapthylphosphine) palladium (II) chloride, [1,2-(bis-diphenylphosphino)ethane] palladium (II) chloride, bis(tributylarsine) palladium (II) bromide, bis(trioctylphosphine) palladium (II) nitrate and the like, complexes with phosphates and phosphites, e.g., bis(trioctylphosphite palladium (II) nitrate, tetrakis(triphenylphosphite) palladium (O), bis(triphenylphosphite) palladium (II) chloride and the like: complexes with tridentate ligands of the type outlined above may also be used. Various other palladium compounds which may be used include palladium (II) alkanoates, e.g., palladium (II) acetate, bis(triphenylphosphine) palladium carbonate, palladium (II) butyrate, palladium (II) hexanoate and the like; the palladium (II) cycloalkanecarboxylates, e.g., palladium (II) cyclohexanecarboxylate and the like; palladium (II) arylcarboxylates, e.g., palladium (II) benzoate, palladium (II) monomethylphthalate and the like; complexes with alkyl and aryl nitriles, e.g., bis(benzonitrile) palladium (II) chloride, bis(propionitrile) palladium (II) cyanide and the like; as well as palladium compounds such as palladium (II) bromide, palladium (II) chloride, palladium (II) nitrate, palladium (II) sulfate, ammonium chloropalladite, potassium chloropalladate, potassium chloropalladite, sodium chloropalladite and the like.

Palladium metal in an active form such as palladium black or palladium on a support, such as charcoal, may be used as the source of the catalytic palladium species. Palladium complexes can be generated in situ by reaction of such active forms of palladium with species such as allyl bromide (to give $\pi$-allylpalladium bromide) or trihydrocarbylphosphines, trihydrocarbylphosphites, or trihydrocarbylarsines or mixtures thereof.

For the sake of brevity, this descriptive list has been limited to some of the applicable compounds of palladium. Analogous compounds of platinum are well known and are also effective as catalysts in this process. Ruthenium compounds also have some activity in this invention and are generally added as a ruthenium (III) compound. For several reasons, among them being convenience, the preferred metal is palladium.

While any one of the palladium, platinum or ruthenium compounds previously described can be used as catalysts, improved results can be obtained by the addition of certain ligands as catalyst modifiers, in the cases of compounds which do not contain such ligands. These ligands or modifiers can be reacted with the metal-containing compound in a separate reaction and added to the reaction mixture of the diene with water and carbon dioxide or it can be added directly to the reactant mixture to yield an active catalyst species in situ.

Even in the cases of the preformed complexes increased amounts of ligand can result in an improved process.

The modifiers can be selected from the trihydrocarbyl phosphines (the trialkyl phosphines: e.g., tri n-octylphosphine, tributylphosphine, dimethyl-n-octylphosphine, tricyclohexylphosphine and the like; triarylphosphine, e.g., triphenylphosphine, tritolylphosphine, diphenyl p-chlorophenylphosphine, tris(p-methoxyphenyl) phosphine, and the like; the tertiary alkaryl phosphines, e.g., diphenylethylphosphine, dimethylphenylphosphine, bis(diphenylphosphino)methane, 1,2-bis(diphenylphosphino)ethane and the like; the trihydrocarbylarsines (the trialkyl, triaryl and alkaryl arsines illustrated by substitution of As for P in the compounds described above) and the trihydrocarbylphosphites (trialkylphosphites, e.g., triethylphosphite, tributylphosphite, tricyclohexylphosphite, tri(2-ethylhexyl)phosphite, tris(2-hydroxyethyl)phosphite, tris(2-ethoxyethyl)phosphite and the like; as well as certain bicyclic phosphites of the general structure shown below.

Compounds with both phosphorus to oxygen and phosphorus to carbon bonds such as diethoxyphenylphosphine

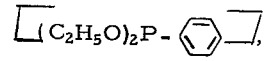

ethoxydiphenylphosphine, dimethoxyphenylphosphine, diisopropoxyphenylphosphine, bis(2-butoxy)-phenylphosphine, diphenoxyethylphosphine, and the like can be used.

Also bicyclic compounds can be used such as

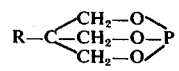

where R can represent a hydrogen; or an alkyl group such as methyl, ethyl, nonyl and the like; or an aryl group such as phenyl, tolyl, naphthyl and the like; or a functionally substituted alkyl group such as hydroxymethyl, ethoxymethyl, phenoxymethyl, hydroxylethyl, hydroxypentyl, acetoxymethyl, acetoxypentyl and the like. These phosphites can be visualized as being derived as the products of esterification of phosphorus acid$((HO)_3P)$ with triols of the general formula R-C-$(CH_2OH)_3$. Phosphites derived in this manner from alcohols of the general formula R-C-$(CR'_2OH)_3$ where R' is some other carbon containing radical or a hydrogen are also useful modifiers in this system.

Another type of bicyclic phosphite that is useful includes those compounds of the general type shown below where R and R' can be hydroxyl, alkyl, aryl, alkoxy or aryloxy, as described for R above.

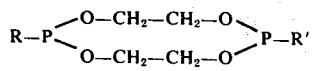

Other phosphites that are useful modifiers are the triarylphosphites, e.g., triphenylphosphite, tri(p-chlorophenyl)phosiphite, tri(1-naphthyl)-phosphite and the like. Mixed alkylarylphosphites can be prepared and used. Because of the methods of synthesis and the relatively facile exchange of groups, it is difficult to prepare discrete compounds in high yield; the mixtures are suitable for use as modifiers if so desired.

Because of considerations such as solubility, it may be advantageous to use mixtures of various hydrocarbylphosphines, for example, mixtures of phosphines and/or arsines and/or phosphites.

These modifiers may be added to the reaction mixture in quantities such that the ratio of the total number of moles of modifiers of all kinds (whether added as components of the palladium, platinum or ruthenium catalyst or added separately) to palladium, platinum or ruthenium can vary, for example, from 200:1 and higher and 1:10 and lower, preferably from 50:1 to 0.2:1, most preferably from 20:1 to 1:1.

The catalyst is employed in catalytically significant quantities. A catalyst concentration based on the total reaction mixture in the range from about 0.000001 molar and lower to about one molar and higher is suitable. A catalyst concentration in the range from about 0.0001 to about 0.1 molar is preferred. For optimum results, the nature of the reactants, the operative conditions under which the reaction is conducted, the solvent characteristics, and other factors, will largely determine the desired catalyst concentration.

The reaction can be conducted with the catalyst absorbed on a solid support, e.g., silica, alumina, silica-alumina, asbestos, activated carbon and the like. The supported catalyst may be used as a heterogeneous catalyst in a liquid phase reaction, in a trickling phase reactor, in which one or more of the reactants may be introduced as a gas, and if the physical properties of all the components of the reaction mixture are suitable, it may be used in a gas phase reaction. The amount of catalyst on the support can be varied over a wide range, e.g., 0.001 to 10 weight percent of the catalyst based on the weight of the catalyst and support.

The process of the invention is conducted in the presence or absence of solvent. In the modification wherein solvent is employed, solvents that are suitable are those that are capable of dissolving the reactants, catalyst, and catalyst promoter and are inert to the reactants or give an initial product which is inert to the reactants and will still dissolve the reactants, the catalyst, and the catalyst promoter. Exemplary solvents are dialkylethers such as diethylether and the like; cyclic ethers such as dioxane, tetrahydrofuran, dioxolane and the like; and lower alkyl ethers of polyhydric alcohols or polyoxyalkylene glycols such as ehtylene glycol dimethyl ether, tetraethylene glycol dimethyl ether and the like; alcohols such as t-butanol, dimethylethylcarbinol, ethanol, iso-butanol, iso-propanol, neopentylalcohol, 1,1,1-trifluoroethanol, 1,1,1-trifluoro-2-propanol, and the like; alkyoxy and aryloxypoly(alkenoxy) alkanols such as (Union Carbide Trade Name) TERGITOL NPX, X-H, UCON 50-HB - 50 and the like; ketones such as acetone, methylethylketone, diethylketone, methylisopropylketone and the like; alkanoic acid amides such as acetamide, propionamide and the like; N,N dialkylalkanoic acid amides such as N,N-dimethylformamide, N,N dimethylacetamide, N,N diethylacetamide, and the like; pyridine derivatives such as pyridine, methylpyridines (picolines), methylethylpyridine, and the like; sulfoxides such as dimethylsulfoxide and the like; sulfones such as tetrahydrothiophene-1,1-dioxide and the like; phosphoric acid amides such as hexamethylphosphoramide and the like; nitriles such as acetonitrile, propionitrile, benzonitrile and the like; esters such as ethylacetate, methylpropionate, methylbenzoate and the like; aromatic compounds such as benzene, toluene, ethylbenzene, xylene and the like; aliphatic hydrocarbons such as butane, hexane, heptane and the like; olefins such as butenes, hexenes, 1,7-octadiene and the like. Many of these solvents are effective alone but may also be mixed with others herein mentioned if some advantage can be attained by so doing.

In certain instances, a heterogeneous catalyst can be used in the reaction and in this instance any solvent used would not necessarily dissolve the catalyst. Normally, vigorous stirring is used to facilitate contact of the catalyst and the reactant.

The reaction can be run in the presence of various compounds that are known to interact with the metal and these will not seriously affect the final nature of the distribution within the reaction mixture. Some of these compounds are known to form stable complexes with the active metals and they can serve as additional protective ligands to prevent the deposition of metal during the course of the reaction and in the subsequent treatment to prepare the catalyst for recycle. Examples of these compounds are bidentate nitrogen containing materials such as 2,2'-dipyridyl, 1,10-phenanthroline, dimethylgyoxime, tetramethylurea, 8-hydroxyquinoline, 4,4'-methylenedianaline, and the like; imides such as succinimide, N-methylsuccinimide, phthalimide, N-methylphthalimide, and the like; tertiary amines such as trialkylamines, e.g., trimethylamine, triethylamine, tri-n-octylamine, dimethyldodecylamine, and the like; functionally substituted trialkylamines such as 2-dimethylaminoethanol, 3-dimethylamino-1-propanol, 2-dimethylaminoethylacetate, N-hydroxyethyl piperidine, N-methyldiethanolamine, triethanolamine, 2-dimethylaminoethyl ethyl ether, 2-(dimethylamino)-1-ethyl phenyl ether and the like; cyclic amines such as N-alkylpiperidines, (N-methyl piperidine, N-ethyl, N-octyl, N-benzyl, etc.) (N-alkylpyrrolidines (as above), N-alkylmorpholines (as above), N-alkyl tetrahydro-o-isoxazines, N-alkyldecahydroquinolines, N-alkyl octahydroindoles, N,N'-dialkyltetrahydrooxadiazenes and the like; tertiary acyclic aliphatic diamines such as N,N,N',N'-tetramethyl-1,3-butanediamine, N,N,N',N'-tetramethyl-1,2-ethanediamine, N,N,N',N'-tetramethyl-1,6-hexanediamine and the like; the cyclic diamines and polyamines such as N,N'-dialkylpiperazines, e.g., N,N'-dimethylpiperazine, N,N'-dibutylpiperazine, N,N'-butylmethylpiperazine, N-(2-hydroxyethyl)-N'-methylpiperazine, N,N'-bis(2-hydroxyethyl)piperazines, N-(2-acetoxyethyl)-N'-methylpiperazine; N,N'-disubstituted decahydroquinazolines, N,N'-disubstituted decahydropyridopyridines and the like. The substituents implied are the same and similar ones as those outlined for piperazine. Polyamines such as hexamethylenetetramine; the bicyclic trisubstituted amines and diamines such as quinuclidine and triethylenediamine and the like are also effective.

The materials mentioned above can be used in the presence of the catalyst modifiers previously described. A great number of combinations of modifiers can successfully aid this synthesis.

The reactions of the present invention can be carried out by charging the catalyst, the solvent, the water, the carbon dioxide and, if desired, the modifiers to a pressure-vessel and introducting the butadiene to the vessel. Other orders of addition can also be convenient and have been found to yield the product. The reaction can be carried out at temperatures of −5°C. to 200°C., although the temperature is not a critical part of the invention. Preferred reaction temperatures are 20°C. to 180°C., most desirably from 50°C. to 150°C. The reaction can be carried out at autogeneous pressures, or higher if desired as well as at atmospheric pressure or below if it presents any advantages. After the reaction, the organic products may be recovered by any standard technique or special techniques known to those skilled in the art and the catalyst recycled for further use.

In the reaction butadiene maay be replaced with other 1,3-dienes to form substituted octadienol alcohols. Suitable dienes are isoprene, piperylene, 1,3-hexadiene, 2,3-dimethylbutadiene, chloroprene, methoxybutadiene, and similar compounds. These materials can be used alone or in mixtures with other compounds.

EXAMPLES

Typical experiments were carried out in 50 cc Pyrex pressure tubes to which the reactants were charged and the tube sealed by using an ordinary bottle capper. Heavy rubber seals were sometimes used along with caps containing openings through which samples could be removed for vapor phase chromatographic analysis. Typical amounts charged to a tube were 2.0 gram butadiene, 0.8 gram carbon dioxide, 0.6 gram water, 10 cc. of solvent, 0.15–0.25 mmole of palladium acetylacetonate and 0.30–0.75 mmole of triphenylphosphine. The charged tubes were placed in an oil or water bath preheated to the desired temperature.

Larger runs were made in a 3-pint Chemco glass pressure reactor which was equipped with a stirrer. The reactant mixture was heated by passing water or steam at the desired temperature through an internal heating coil. A dip tube in the reaction vessel allowed periodic samples to be removed for analysis.

The results of some experiments are shown in Tables I - X. These are meant to illustrate the invention and are not presented as a definition of the limits of the invention.

The examples listed in Table I show the effect of solvents on the reaction of butadiene with water to produce octadienol.

TABLE I

| | | | REACTION OF BUTADIENE WITH WATER[a] | | | | |
|---|---|---|---|---|---|---|---|
| Run No. | Solvent | P/Pd | Temp. | Time (hrs.) | % Yield Octadienol | 1:3[c] | % Yield Octatriene |
| 1 | Dioxane | 1 | 70°C. | 20 | 4 | 95:5 | 17 |
| 2 | DMAC[b] | 1 | 70°C. | 1.5 | 17 | 92:8 | 5 |
| 3 | Dioxane | 3 | 90°C. | 2.5 | 10 | 92:8 | 60 |
| 4 | t-Butanol | 1 | 90°C. | 2.5 | 4 | 90:10 | 18 |
| 5 | DMAC | 1[d] | 90°C. | 2.0 | 10 | 90:10 | 10 |
| 6 | DMAC | 4[e] | 90°C. | 20.0 | 10 | 95:5 | 30 |

[a]All reactions were run in 50 cc. Pyrex pressure tubes using 0.25 mmole of palladium acetylacetonate as the palladium source and triphenylphosphine as the phosphorus source. The amount of solvent used was 10 ml.
[b]N,N-Dimethylacetamide.
[c]Refers to the ratio of octa-2,7-dien-1-ol to octa-1,7-dien-3-ol.
[d]Triphenylarsine was used as the ligand.
[e]tris(Dimethylaminomethyl)phosphine was used as the phosphorous source.

The examples listed in Table II show the effect of various alcohols in increasing the yield of octadienol in the reaction of butadiene and water.

TABLE II

| | | ALCOHOL ASSISTED REACTION OF WATER WITH BUTADIENE[a] | | | | | | | |
|---|---|---|---|---|---|---|---|---|---|
| | | | Charge (mmoles) | | | Molar Ratio | | Time | % Yield | |
| Run No. | Alcohol | Solvent | BD | Water | Alcohol | P/Pd | Temp. | (hrs.) | Octadienol | 1:3[b] |
| 1 | —OH | Dioxane | 55 | 55 | — | 1 | 70°C. | 20 | 4 | 95:5 |
| 2 | CF$_3$CHCH$_3$ | Dioxane | 55 | 55 | 8.7 | 1 | 70°C. | 20 | 16 | 90:10 |
| 3 | CF$_3$CH$_2$OH | Dioxane | 55 | 55 | 5.0 | 1 | 70°C. | 20 | 22 | 85:15 |
| 4 | (CH$_3$)$_3$C—CH$_2$OH | Dioxane | 55 | 37 | 9.0 | 1 | 70°C. | 20 | 40 | 90:10 |
| 5 | (CH$_3$)$_3$C—CH$_2$OH | Dioxane | 55 | 37 | 9.0 | 3 | 70°C. | 20 | 30 | 65:35 |
| 6 | C$_2$H$_5$OH | — | 55 | 55 | 110 | 1 | 70°C. | 1.5 | 12 | 93:17 |
| 7 | (CH$_3$)$_2$—CHCH$_2$OH | — | 55 | 55 | 95 | 1 | 70°C. | 1.5 | 25 | 82:18 |

[a]All reactions were run in 50 cc. Pyrex pressure tubes using 0.25 mmole of palladium acetylacetonate as the palladium source and triphenylphosphine as the phosphorous source. The amount of solvent used was 10 ml.
[b]Refers to the ratio of octa-2,7-dien-1-ol to octa-1,7-dien-3-ol.

The examples listed in Table III show the effect of varying the watercarbon dioxide-butadiene ratio in the reaction of butadiene and water in the presence of tertiary butanol.

TABLE III t-BUTANOL SOLVENT[a]

| Run No. | BD | Molar Ratios CO$_2$ | H$_2$O | t-BuOH | °C Temp. | Time (hrs.) | mmoles Pd | P/Pd | % Yield Octa-dienol | 1:3[f] Ratio | % Yield Octa-triene |
|---|---|---|---|---|---|---|---|---|---|---|---|
| 1 | 1 | 0.3 | 1.0 | 1.1 | 105 | 2.0 | 2.0 | 2 | 76 | 75:25 | 12 |
| 2 | 1 | 0.3 | 0.9 | 1.9 | 100 | 0.75 | 4.0 | 1 | 62 | 91:9 | 9 |
| 3 | 1 | 0.07 | 1.0 | 3.0 | 95 | 2.0 | 7.0 | 1 | 68 | 88:12 | 21 |
| 4 | 1 | 0.07 | 1.0 | 3.0 | 75 | 3.0 | 7.0 | 1 | 62 | 96:4 | 7 |
| 5 | 1[b] | 0.4 | 1.2 | 1.2 | 104 | 3.0 | 2.2 | 2 | 63 | 63:37 | 22 |
| 6 | 1[b] | 0.4 | 1.2 | 1.2 | 75 | 4.0 | 2.2 | 1 | 51 | 92:8 | 2 |
| 7 | 1 | 3.4 | 6.4 | 4.2 | 105 | 3.0 | 9.0 | 1 | 49 | 68:32 | 22 |
| 8 | 1 | 1.4 | 2.7 | 3.0 | 85 | 1.0 | 3.3 | 2.8 | 82 | 78:22 | 3 |
| 9 | 1 | 1.1 | 2.0 | 1.8 | 78 | 4.7 | 1.6 | 2.2 | 70 | 85:15 | nil |
| 10 | 1 | 1.0 | 1.0 | 2.1 | 80 | 3.0 | 5.0[c] | 4.0 | 52 | 50:50 | 4 |
| 11 | 1 | 1.0 | 1.9 | 6.0 | 70 | 3.0 | 4.5 | —[d] | 44 | 79:21 | nil |
| 12 | 1 | 0.1 | 1.9 | 3.0 | 70 | 3.0 | 1.9 | —[d] | 40 | 95:5 | nil |
| 13 | 1 | 0.3 | 0.9 | 1.8 | 100 | 0.5 | 4.0 | 1.0 | 62 | 90:10 | 8 |
| 14 | 1 | 0.5 | 1.5 | 2.0 | 85 | 2.0 | 2.0[e] | 3.0 | 68 | 83:17 | 1 |

[a] All runs were made in a 3-pint Chemco pressure glass reactor and were stirred with a mechanical stirrer. Palladium acetylacetonate was used as the palladium source and triphenyl phosphine was used as the phosphorus source unless otherwise noted.
[b] The butadiene was charged as the C$_4$ stream from an olefins plant.
[c] The Pd was charged as PdCl$_2$.
[d] The catalyst was charged as $\phi_3P$–PdCO$_3$–$\phi_3P$.
[e] The Pd was charged as palladium acetate.
[f] The ratio of octa-2,7-dien-1-ol to octa-1,7-dien-3-ol.

The examples listed in Table IV show the effect of varying the reactant and catalyst ratios in the reaction of butadiene with water in presence of acetone solvent.

The examples listed in Table V show the effect of varying reactant and catalyst ratios in the reaction of butadiene with water in the presence of acetonitrile solvent.

TABLE IV

SYNTHESIS OF OCTADIENOL IN ACETONE SOLVENT[a]

| Run No. | BD | Molar Ratios CO$_2$ | H$_2$O | Acetone | mmoles Pd | P/Pd | Temp. | Time | % Yield Octa-dienol | 1:3[e] | % Yield Octa-triene |
|---|---|---|---|---|---|---|---|---|---|---|---|
| 1 | 1 | 1.6 | 2.4 | 2.0 | 2.6 | 3.9 | 78 | 3.0 | 75 | 87:13 | 2 |
| 2 | 1 | 0.5 | 1.6 | 1.8 | 1.7 | 3.7 | 90 | 3.0 | 77 | 92:8 | 8 |
| 3 | 1 | 1.4 | 2.5 | 3.0 | 3.3 | 3.7 | 90 | 1.0 | 71 | 88:12 | 3 |
| 4 | 1 | 1.4 | 1.6 | 3.0 | 1.7 | 2.7 | 90 | 2.0 | 84 | 88:12 | 3 |
| 5 | 1 | 0.5 | 1.5 | 3.7 | 4.0 | 4.0[b] | 80 | 2.0 | 61 | 84:16 | 5 |
| 6 | 1 | 0.5 | 1.5 | 3.7 | 4.0 | 2.0[c] | 80 | 2.0 | 61 | 96:4 | 1 |
| 7 | 1 | 0.5 | 1.5 | 3.7 | 4.0 | 4.0[d] | 80 | 2.0 | 43 | 95:5 | 8 |

[a] Unless otherwise noted the Pd was charged as palladium acetylacetonate and the phosphine was charged as triphenylphosphine.
[b] The source of Pd and P was $(\phi_3P)_4Pd$.

[c] The source of Pd and P was 
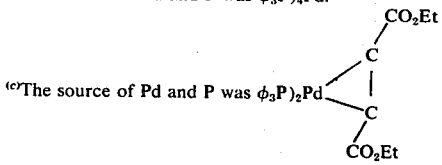

[d] The ligand used was bis(2-butoxy)phenylphosphine, 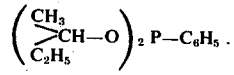

[e] The ratio of octa-2,7-dien-1-ol to octa-1,7-dien-3-ol

TABLE V

SYNTHESIS OF OCTADIENOL IN ACETONITRILE SOLVENT[a]

| Run No. | BD | Molar Ratios CO$_2$ | H$_2$O | CH$_3$CN | mmoles Pd | P/Pd | Temp. | Time (hrs.) | % Yield Octa-dienol | 1:3[b] | % Yield Octa-triene |
|---|---|---|---|---|---|---|---|---|---|---|---|
| 1 | 1 | 0.5 | 1.5 | 5.4 | 4.0 | 2.6 | 80 | 2.0 | 54 | 93:7 | 2 |
| 2 | 1 | 0.5 | 1.5 | 3.8 | 4.0 | 1.3 | 80 | 2.0 | 61 | 95:5 | 9 |
| 3 | 1 | 0.5 | 0.75 | 5.4 | 4.0 | 5.2 | 80 | 2.0 | 55 | 90:10 | 1 |
| 4 | 1 | 0.5 | 1.5 | 5.4 | 4.0 | 10.4 | 80 | 2.0 | 58 | 73:27 | 11 |
| 5 | 1 | 0.3 | 1.5 | 3.7 | 2.5 | 7.0 | 85 | 2.0 | 60 | 85:15 | 5 |

[a] The palladium was charged as palladium acetylacetonate and the phosphine was charged as triphenylphosphine.
[b] Refers to the molar ratio of octa-2,7-dien-1-ol to octa-1,7-dien-3-ol.

The examples listed in Table VI show the effect of varying reactant and catalyst ratios in the reaction of butadiene with water in the presence of various other solvents.

The examples listed in Table VIII show the effect of conducting the reaction of butadiene and water in the presence of polydentate nitrogen containing ligands.

TABLE VIII

SYNTHESIS OF OCTADIENOL IN THE PRESENCE OF POLYDENTATE N-CONTAINING LIGANDS[a]

| Run No. | BD | Molar Ratio $CO_2$ | $H_2O$ | Acetone | mmoles Pd | P/Pd | N Ligand | Structure of N Ligand | Temp. | Time (hrs.) | % Yield Octa-dienol | 1:3[b] | % Yield Octa-triene |
|---|---|---|---|---|---|---|---|---|---|---|---|---|---|
| 1 | 1 | 0.5 | 1.5 | 3.7 | 4.0 | 2.5 | 4.0 | 2,2' bipyridyl | 80 | 2.0 | 70 | 86:14 | 1 |
| 2 | 1 | 0.5 | 1.5 | 3.7 | 4.0 | 2.5 | 10.0 | 2,2' bipyridyl | 80 | 2.0 | 40 | 82:18 | 3 |
| 3 | 1 | 0.5 | 1.5 | 3.7 | 4.0 | 2.5 | 1.0 | 8-Hydroxy quinoline | 80 | 2.0 | 57 | 84:16 | 4 |
| 4 | 1 | 0.5 | 1.5 | 3.7 | 4.0 | 2.5 | 4.0 | 8-Hydroxy quinoline | 80 | 2.0 | 48 | 86:14 | 3 |
| 5 | 1 | 0.5 | 1.5 | 3.7 | 4.0 | 2.5 | 4.0 | 4,4'methyl-ene dianiline | 80 | 2.0 | 68 | 88:12 | 10 |
| 6 | 1 | 0.5 | 1.5 | 3.7 | 4.0 | 2.5 | 4.0 | Dimethyl-glyoxime | 80 | 2.0 | 50 | 82:18 | 4 |
| 7 | 1 | 0.3 | 2.3 | 2.0 | 3.6 | 3.5 | 4.0 | Succinimide | 80 | 2.0 | 44 | 92:8 | 3 |

[a]The palladium was charged as palladium acetylacetonate and the P as triphenylphosphine.
[b]Refers to the ratio of octa-2,7-dien-1-ol to octa-1,7-dien-3-ol.

The examples listed in Table IX show the effect of

TABLE VI

SYNTHESIS OF OCTADIENOL IN OTHER SOLVENTS[a]

| Run No. | BD | Molar Ratios $CO_2$ | $H_2O$ | Solvent | mmoles Pd | P/Pd | Solvent | Temp. | Time (Hrs.) | % Yield Octa-dienol | 1:3[c] | % Yield Octa-triene |
|---|---|---|---|---|---|---|---|---|---|---|---|---|
| 1 | 1 | 0.4 | 1.3 | 2.4 | 3.4 | 2.6 | Pyridine | 80 | 2.0 | 50 | 61:39 | 10 |
| 2 | 1 | 0.3 | 1.0 | 1.8 | 2.7 | 5.2 | Pyridine | 80 | 2.0 | 40 | 54:46 | 13 |
| 3 | 1 | 0.5 | 1.5 | 2.7 | 4.0 | 1.3 | Pyridine | 80 | 2.0 | 50 | 75:25 | 14 |
| 4 | 1 | 1.0 | 1.8 | 5.0 | 13.0 | 1.0 | DMAC[b] | 90 | 3.0 | 40 | 70:30 | 10 |
| 5 | 1 | 0.5 | 1.5 | 2.0 | 2.0 | 3.0 | Dioxane | 85 | 3.0 | 74 | 66:34 | 14 |

[a]The palladium was charged as palladium acetylacetonate and the phosphorous as triphenylphosphine.
[b]N,N Dimethylacetamide.
[c]Refers to the ratio of octa-2,7-dien-1-ol to octa-1,7-dien-3-ol.

The examples listed in Table VII show the effect of conducting the reaction of butadiene and water in the presence of a tertiary amine.

conducting the reaction of butadiene with water in the presence of alkyoxy and aryloxypoly(alkylenoxy) alkanols.

TABLE VII

SYNTHESIS OF OCTADIENOL IN THE PRESENCE OF TERTIARY AMINES[a]

| Run No. | BD | Molar Ratios $CO_2$ | $H_2O$ | Amine | Solvent | mmoles Pd | P/Pd | Temp °C. | % Yield Octa-dienol | 1:3[b] | % Yield Octa-triene |
|---|---|---|---|---|---|---|---|---|---|---|---|
| 1 | 1 | 2.9 | 1.8 | 1.3[c] | Dioxane | 13 | 3 | 90 | 65 | 42:58 | 30 |
| 2 | 1 | 1 | 3.3 | 0.55[c] | Dioxane | 12.5 | 3 | 90 | 85 | 75:25 | 15 |
| 3 | 1 | 1 | 1.8 | 0.7[c] | Dioxane | 13 | 3 | 60 | 85 | 31:69 | 10 |
| 4 | 1 | 1 | 1.8 | 1.1[d] | Dioxane | 13 | 3 | 90 | 55 | 90:10 | 10 |
| 5 | 1 | 1 | 1.8 | 0.7[c] | Dioxane | 13 | 5[f] | 90 | 6 | 90:10 | 25 |
| 6 | 1 | 1 | 1.8 | 0.7[c] | Dioxane | 13 | 2[f] | 60 | 66 | 95:5 | 8 |
| 7 | 1 | 0.1 | 1.7 | 0.1[c] | Dioxane | 6.5 | 3 | 90 | 74 | 70:30 | 21 |
| 8 | 1 | 1 | 1.8 | 0.7[c] | t-Butanol | 13 | 1 | 90 | 63 | 67:33 | 19 |
| 9 | 1 | 1 | 1.8 | 0.7[c] | DMAC[g] | 13 | 1 | 90 | 45 | 95:5 | 20 |
| 10 | 1 | 1 | 3.3 | 0.55 | Dioxane | 14 | 2[h] | 90 | 58 | 73:27 | 30 |
| 11 | 1 | 0.5 | 1.5 | 0.5[d] | Acetone | 4 | 2.6 | 80 | 42 | 73:27 | 15 |
| 12 | 1 | 0.5 | 1.5 | 0.25[d] | Acetone | 4 | 2.6 | 80 | 70 | 76:24 | 9 |
| 13 | 1 | 0.5 | 1.5 | 0.25[c] | Acetone | 4 | 2.6 | 80 | 80 | — | 5 |
| 14 | 1 | 0.5 | 1.5 | 0.13[c] | Acetone | 4.0 | 2.6 | 80 | 80 | — | 5 |
| 15 | 1 | 0.5 | 1.5 | 0.06[e] | Acetone | 4.0 | 2.6 | 80 | 70 | 73:27 | 10 |
| 17 | 1 | 0.5 | 1.5 | — | Acetone | 4.0 | 2.6 | 80 | 75 | 89:11 | 2 |

[a] The runs were made in 50 cc glass pressure tubes using typical amounts as described in the introduction to this section. Unless otherwise noted palladium acetylacetonate was used as the source of palladium and triphenylphosphine was used as the phosphorous containing compound. The reactions were run for 2–3 hours.
[b] Refers to the ratio of octa-2,7-dien-1-ol to octa-1,7-dien-3-ol.
[c] N,N,N',N' tetramethyl-1,3-butanediamine.
[d] Triethylamine.
[e] Triethylenediamine (DABCO).
[f] Trimethylolpropane phosphite

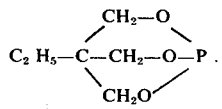

[g] N,N Dimethylacetamide.
[h] 1,2-bis(diphenylphosphino)ethane.

TABLE IX

SYNTHESIS OF OCTADIENOL IN THE PRESENCE OF ALKYOXY AND ARYLOXYPOLY(ALKYLENOXY)ALKANOLS[a]

| Run No. | BD | Molar Ratio $CO_2$ | $H_2O$ | Acetone | Wt. % in Solvent Surfactant | mmoles Pd | P/Pd | % Yield Octadienol | 1:3[b] | % Yield Octatriene | Union Carbide Surfactant |
|---|---|---|---|---|---|---|---|---|---|---|---|
| 1 | 1 | 0.5 | 1.5 | 3.7 | 11 | 4.0 | 2.6 | 69 | 85:15 | 7 | NPX[c] |
| 2 | 1 | 0.5 | 1.5 | 3.7 | 20 | 4.0 | 2.6 | 71 | 86:14 | 5 | NPX |
| 3 | 1 | 0.5 | 1.5 | 3.7 | 10 | 4.0 | 2.6 | 77 | 82:18 | 10 | MIN-FOAM[d] |
| 4 | 1 | 0.5 | 1.5 | 3.7 | 20 | 4.0 | 2.6 | 70 | 82:18 | 9 | MIN-FOAM |
| 5 | 1 | 0.5 | 1.5 | 3.7 | 10 | 4.0 | 2.6 | 60 | 93:7 | 3 | X-H[e] |
| 6 | 1 | 0.5 | 1.5 | 3.7 | 20 | 4.0 | 2.6 | 50 | 92:8 | 4 | X-H |
| 7 | 1 | 0.5 | 1.5 | 3.7 | — | 4.0 | 2.6 | 75 | 89:11 | 2 | — |

[a] The palladium was charged as palladium acetylacetonate and the phosphorous as triphehylphosphine. All reactions were run at 80° for two hours.
[b] Refers to the ratio of octa-2,7-dien-1-ol to octa-1,7-dien-3-ol.
[c] NPX - The hydrophobe is nonylphenol and the hydrophile portion is an average of 10.5 ethylene oxide units.
[d] MIN-FOAM - This is a $C_{11}$–$C_{15}$ linear alcohol that is etherified with an ethyl group.
[e] X-H - A polyalkyleneglycol ether.

The examples listed in Table X show the effect of conducting the palladium catalyzed reaction of butadiene with water in the presence of other transition metals.

TABLE X

SYNTHESIS OF OCTADIENOL IN THE PRESENCE OF OTHER METALS[a]

| Run No. | BD | Molar Ratio $H_2O$ | $CO_2$ | t-BuOH | Pd | mmoles $\phi_3$P/Pd | Metal | % Octadienol | 1:3[h] | Octatriene |
|---|---|---|---|---|---|---|---|---|---|---|
| 1 | 1 | 1 | 1 | 2.0 | 2.5[b] | 2/1 | 2.5 | 79 | 75:25 | 7 |
| 2 | 1 | 1 | 1 | 2.0 | 2.5[c] | 2/1 | 2.5 | 70 | 77:23 | 6 |
| 3 | 1 | 1 | 1 | 2.0 | 2.5[d] | 2/1 | 2.5 | 62 | 54:46 | 11 |
| 4 | 1 | 1 | 1 | 2.0 | 2.5[e] | 2/1 | 2.5 | 63 | 60:40 | 8 |
| 5 | 1 | 1 | 1 | 2.0 | 2.5[f] | 2/1 | 2.5 | 74 | 76:24 | 5 |
| 6 | 1 | 1 | 1 | 2.0 | 2.5[g] | 2/1 | 2.5 | 78 | 76:24 | 5 |

[a] All reactions run for three hours at 70–80°.
[b] The compound charged was Pd Ni (OAc)$_4$. HOAc . $H_2O$.
[c] The compound charged was Pd Co (OAc)$_4$ . 2HOAc . $2H_2O$
[d] The palladium was charged as palladium acetylacetonate and the nickel was charged as nickel acetylacetonate.
[e] The palladium was charged as palladium acetylacetonate and the cobalt was charged as cobalt acetylacetonate.
[f] The palladium was charged as palladium acetylacetonate and the nickel as nickel (II) acetate tetrahydate.
[g] The palladium was charged as palladium acetylacetonate and the metal as cobalt (II) acetate tetrahydrate.
[h] Refers to the ratio of octa-2,7-dien-1-ol to octa-1,7-dien-3-ol.

RECYCLE EXPERIMENTS

There was charged to a three pint Chemco reactor 54 g. (1.0 mole) of butadiene, 27 g. (1.5 moles) of water, 22 g. (0.50 moles) of carbon dioxide, 148 g. (2.0 moles) of t-butanol, 15 g. of di n-octylether (0.06 mole), 0.6 g. (0.002 mole) of palladium acetylacetonate, and 1.6 g. (0.006 mole) of triphenylphosphine. This mixture was heated to 85° and maintained at that temperature for 2 hours to give 30 g. of octa-2,7-dien-1-ol (b. pt. 199°C), 10 g. of octa-1,7-dien-3-ol (b. pt. 177°C), 2 g. of 1,3,7-octatriene and 1 g. of bis-(octadienyl)ethers. The reaction mixture was passed through a long tube evaporator (LTV) at 100° and 10 mm pressure. The solvent and product were taken and a "residue" material containing some octadienol as well as the ethers was recovered. This residue was recharged to the reactor along with 54 g. of butadiene, 27 g. of water, 22 g. of carbon dioxide, and 148 g. of t-butanol. The mixture was reacted at 85° for 2 hours to yield 36 g. of octa-2,7-dien-1-ol, 5 g. of octa-1,7-dien-3-ol, 1 g. of 1,3,7-octatriene, and 2 g. of bis-(octadienyl) ethers. This material was passed through the LTV at 100° and 10 mm to remove the solvent and octadienol and the "residue" material was recycled to the reactor along with a fresh charge of the reactants. After 2 hours at 85° the reaction yielded 36 g. of octa-2,7-dien-1-ol, 5 g. of octa-1,7-dien-3-ol, 1 g. of 1,3,7-octatriene and 1 g. of bis-(octadienyl) ethers.

There was charged to the three pint Chemco reactor 54 g. (1.0 mole) of butadiene, 25 g. (1.4 moles) of water, 22 g. (0.50 mole) of carbon dioxide, 174 g. (3.0 moles) of acetone, 1.0 g. (0.003 mole) of palladium acetylacetonate, and 2.4 g. (0.009 mole) of triphenylphosphine. This mixture was heated to 80°C for two hours and yielded 30 g. of octa-2,7-dien-1-ol, 7 g. of octa-1,7-dien-3-ol, 3 g. of 1,3,7-octatriene, and 2 g. of bis-(octadienyl) ethers. After adding 15 g. of bis(n-octyl) ether the material was "stripped" of solvent and most of the product by passing it through a long tube evaporator (LTV) at 100° and 10 mm pressure. The "residue" weighed 28 grams and was recycled to the reactor along with a charge of the solvent and the reactants. After 2 hours at 80° the net yield was 27 g. of octa-2,7-dien-1-ol, 5 g. of octa-1,7-dien-3-ol and 1 g. of 1,3,7-octatriene. The reaction mixture was passed through the LTV and the recovered "residue" was recycled to the reactor along with a fresh charge of solvent and the reactants. After 2 hours at 80° the net yield was 29 g. of octa-2,7-dien-1-ol, 4 g. of octa-1,7-dien-3-ol, and 1 g. of 1,3,7-octatriene.

We claim:
1. Process for forming octadienols which comprises forming a reaction mixture containing butadiene, water, a solvent which is at least partially miscible with water and butadiene and carbon dioxide and a catalyst which is a palladium compound complexed with a phosphine ligand, causing the butadiene and water to react at a reaction temperature of from 20°C. to 180°C; to form an octadienol and recovering the octadienol from the reaction mixture; said butadiene, carbon dioxide and water being present in amounts sufficient to produce said octadienol.

2. The process of claim 1 wherein the phosphine is a trihydrocarbyl phosphine.

3. The process of claim 1 wherein the phosphine is a triarylphosphine.

4. The process of claim 3 wherein the triarylphosphine is triphenyl phosphine.

5. The process of claim 1 wherein the molar ratio of carbon dioxide to butadiene in the reaction mixture is from 0.001 to 1000 and the molar ratio of water to butadiene in the reaction mixture is from 0.1 to 1000.

6. The process of claim 5 wherein the molar ratio of carbon dioxide to butadiene is from 0.01 to 25 and the molar ratio of water to butadiene is 0.1 to 10.

7. The process of claim 6 wherein the carbon dioxide to butadiene ratio is 0.05 to 5.0.

8. The process of claim 1 wherein the catalyst is selected from the group of tetrakis (triphenylphosphine) palladium (O), bis(triphenylphosphine) palladium carbonate, palladium acetylacetonate, palladium acetate, and palladium chloride.

9. The process of claim 1 wherein the palladium compound is palladium acetylacetonate and the phosphine is triphenylphosphine.

10. The process of claim 1 wherein the solvent is selected from the group consisting of dioxane, tertiary butanol, N,N-dimethyl acetamide, alkoxypoly(alkylenoxy)alkanols, aryloxypoly(alkylenoxy)alkanols, acetone, acetonitrile, and pyridine.

11. The process of claim 1 in which the catalyst is complexed with a nitrogen-containing polydentate ligand.

12. The process of claim 5 wherein the reaction mixture contains a tertiary amine.

13. The process of claim 11 wherein the polydentate ligand is selected from the group of dimethylglyoxime, 8-hydroxyquinoline and 2,2'-bipyridyl.

14. The process of claim 5 wherein the phosphine is a trihydrocarbylphosphine, the palladium compound is selected from the group of tetrakis(triphenylphosphine)palladium(O), bis(triphenylphosphine)palladium carbonate, palladium acetylacetonate, palladium acetate, and palladium chloride and the solvent is selected from the group consisting of dioxane, tertiary butanol, alkoxypoly(alkylenoxy)alkanols, aryloxypoly(alkylenoxy)alkanols, acetone, acetonitrile, N,N-dimethylacetamide, and pyridine.

15. The process of claim 14 wherein the phosphine is triphenylphosphine.

16. The process of claim 5 wherein the catalyst is a mixture of a palladium compound and a compound of a metal of a group consisting of cobalt, iron, nickel, copper, and tin.

17. Process for forming octadienols which comprises forming a reaction mixture containing butadiene, water, a solvent which is at least partially miscible with water and butadiene, and carbon dioxide and a catalyst which is a palladium compound complexed with a phosphite ligand; causing the butadiene and water to react at a reaction temperature of from 20°C. to 180°C. to form an octadienol and recovering the octadienol from the reaction mixture; said butadiene, carbon dioxide and water being present in amounts sufficient to produce said octadienol.

18. The process of claim 17 wherein the molar ratio of carbon dioxide to butadiene in the reaction mixture is from 0.001 to 1000 and the molar ratio of water to butadiene in the reaction mixture is from 0.1 to 1000.

19. The process of claim 18 wherein the molar ratio of carbon dioxide to butadiene is from 0.01 to 25 and the molar ratio of water to butadiene is 0.1 to 10.

20. The process of claim 13 wherein the phosphine is at least one selected from the group of trihydrocarbylphosphites and bicyclic phosphites of the formulas:

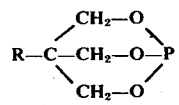

wherein R is selected from the group consisting of hydrogen, alkyl, aryl and substituted alkyl; and

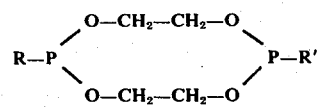

wherein R and R' are selected from the group of hydroxyl, alkyl, aryl, alkoxy and aryloxy.

21. The process of claim 20 wherein the phosphite is one of the formula:

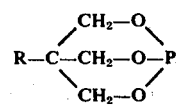

wherein R is selected from the group of hydrogen, alkyl, aryl, and substituted alkyl.

22. The process of claim 21 wherein R is ethyl.

23. The process of claim 19 in which the reaction mixture contains a tertiary amine.

24. The process of claim 23 wherein the tertiary amine is N,N,N',N'-tetramethylbutane-1,3-diamine.

25. The process of claim 19 wherein the solvent is dioxane.

26. The process of claim 21 wherein the reaction mixture contains a tertiary amine, the solvent is dioxane, the molar ratio of water to butadiene in the reaction mixture is from 0.1 to 10 and the molar ratio of carbon dioxide to butadiene in the reaction mixture is from 0.01 to 25.

27. The process of claim 26 wherein the phosphite is trimethylolpropane phosphite, having the formula:

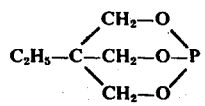

28. The process of claim 27 wherein the palladium compound is palladium acetylacetonate.

29. The process of claim 13 wherein the catalyst is a mixture of a palladium compound and a compound of a metal of the group consisting of cobalt, iron, nickel, copper and tin.

* * * * *

UNITED STATES PATENT OFFICE
CERTIFICATE OF CORRECTION

Page 1 of 2

Patent No. 3,992,456  Dated November 16, 1976

Inventor(s) Kenneth Earl Atkins et al.

It is certified that error appears in the above-identified patent and that said Letters Patent are hereby corrected as shown below:

Column 5, line 10, "phosiphite" should read -- phosphite --

Column 5, line 61, "ehtylene" should read -- ethylene --

Column 7, line 24, "maay" should read -- may --

Column 11-12, TABLE VII, column of TABLE headed "1:3", Run No. 15, "73:27" should read -- 86:14 --

Column 11-12, TABLE VII, column of TABLE headed "% Yield Octatriene", Run No. 15, "10" should read -- 17 --

Column 11-12, TABLE VII, between Run No. 15 and Run No. 17 insert as follows for the various columns
Column headed Run No. insert -- 16 --
Column headed BD insert -- 1 --
Column headed Co insert -- 0.5 --
Column headed H O insert -- 1.5 --
Column headed Amine insert -- .0025(e) --
Column headed Solvent insert -- Acetone --
Column headed m moles Pd insert -- 4.0 --
Column headed P/Pd insert -- 2.6 --
Column headed Temp °C insert -- 80 --
Column headed % Yield Octadienol insert -- 70 --
Column headed 1.3 insert 73:27
Column headed % Yield Octatriene insert -- 10 --

UNITED STATES PATENT OFFICE
CERTIFICATE OF CORRECTION

Patent No. 3,992,456          Dated November 16, 1976

Inventor(s)  Kenneth Earl Atkins et al.

It is certified that error appears in the above-identified patent and that said Letters Patent are hereby corrected as shown below:

Column 13-14, TABLE X, footnote (f), "tetrahydate" should read -- tetrahydrate --

Signed and Sealed this twelfth Day of July 1977

[SEAL]

Attest:

RUTH C. MASON
Attesting Officer

C. MARSHALL DANN
Commissioner of Patents and Trademarks